US00PP21551P3

(12) United States Plant Patent
Danziger

(10) Patent No.: US PP21,551 P3
(45) Date of Patent: Nov. 30, 2010

(54) ***SUTERA* PLANT NAMED 'DANCOP28'**

(50) Latin Name: *Sutera cordata*
Varietal Denomination: DANCOP28

(76) Inventor: Gabriel Danziger, P.O. Box 24, Moshav Mishmar Hashiva, Beit Dagan (IL) 50297

( * ) Notice: Subject to any disclaimer, the term of this patent is extended or adjusted under 35 U.S.C. 154(b) by 0 days.

(21) Appl. No.: 12/383,771

(22) Filed: Mar. 27, 2009

(65) Prior Publication Data

US 2010/0251450 P1 Sep. 30, 2010

(51) Int. Cl.
*A01H 5/00* (2006.01)

(52) U.S. Cl. ..... Plt./485

(58) Field of Classification Search ..... Plt./485
See application file for complete search history.

*Primary Examiner*—June Hwu

(57) ABSTRACT

A new and distinct *Sutera* cultivar named 'DANCOP28' is disclosed, characterized by having a compact, semi-trailing growth habit, and a very well branched, ball-shaped plant. The new variety has very large flowers, with thick petals. Flower color is light blue. The new variety is a Sutera, normally produced as an outdoor garden or container plant.

2 Drawing Sheets

Latin name of the genus and species: *Sutera cordata.*

Variety denomination: 'DANCOP28'.

BACKGROUND OF THE INVENTION

The new *Sutera* cultivar is a product of a planned breeding program conducted by the inventor, Gabriel Danziger, in Moshav Mishmar Hashiva, Israel. The objective of the breeding program was to produce new varieties of *Sutera* for commercial introduction. The seed parent is the unpatented, proprietary seedling variety referred to as *Sutera cordata* 'CV 04-68.' The pollen parent is an unknown *Sutera cordata*, as the new variety is the result of an open pollination in which the male parent cannot be identified. The open pollination occurred in November 2006.

The new variety was discovered in June 2007 by the inventor in a group of seedlings resulting from that crossing, in a commercial greenhouse in Moshav Mishmar Hashiva, Israel. Asexual reproduction of the new cultivar 'DANCOP28' by vegetative cuttings was first performed at a commercial greenhouse in Moshav Mishmar Hashiva, Israel in July 2007. Subsequent propagation has shown that the unique features of this cultivar are stable and reproduced true to type on successive generations.

SUMMARY OF THE INVENTION

The cultivar 'DANCOP28' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'DANCOP28' These characteristics in combination distinguish 'DANCOP28' as a new and distinct *Sutera* cultivar:

1. Compact, semi-trailing growth habit.
2. Very branched, ball-shaped plant.
3. Extra-large flowers with thick petals.

4. Light blue flower color.
5. Medium vigor.

Parental Comparison

Plants of the new cultivar 'DANCOP28' are similar to plants of the seed parent, *Sutera cordata* 'CV-04-68' in most horticultural characteristics, however, plants of the new cultivar 'DANCOP28' have a different color flower.

Commercial Comparison

Plants of the new cultivar 'DANCOP28' can be compared to the commercial variety 'DANCOP24,' U.S. Plant Pat. No. 19,343. Plants of 'DANCOP28' are similar to plants of 'DANCOP24' in most horticultural characteristics, however, plants of the new variety are semi-trailing compared to trailing, causing the new cultivar to form a round plant shape, compared to an elongated plant shape. Additionally, plants of the new variety have thicker petals than 'DANCOP24' and plants of the new variety are less vigorous than plants of 'DANCOP24'.

BRIEF DESCRIPTION OF THE PHOTOGRAPH

Figure 1:
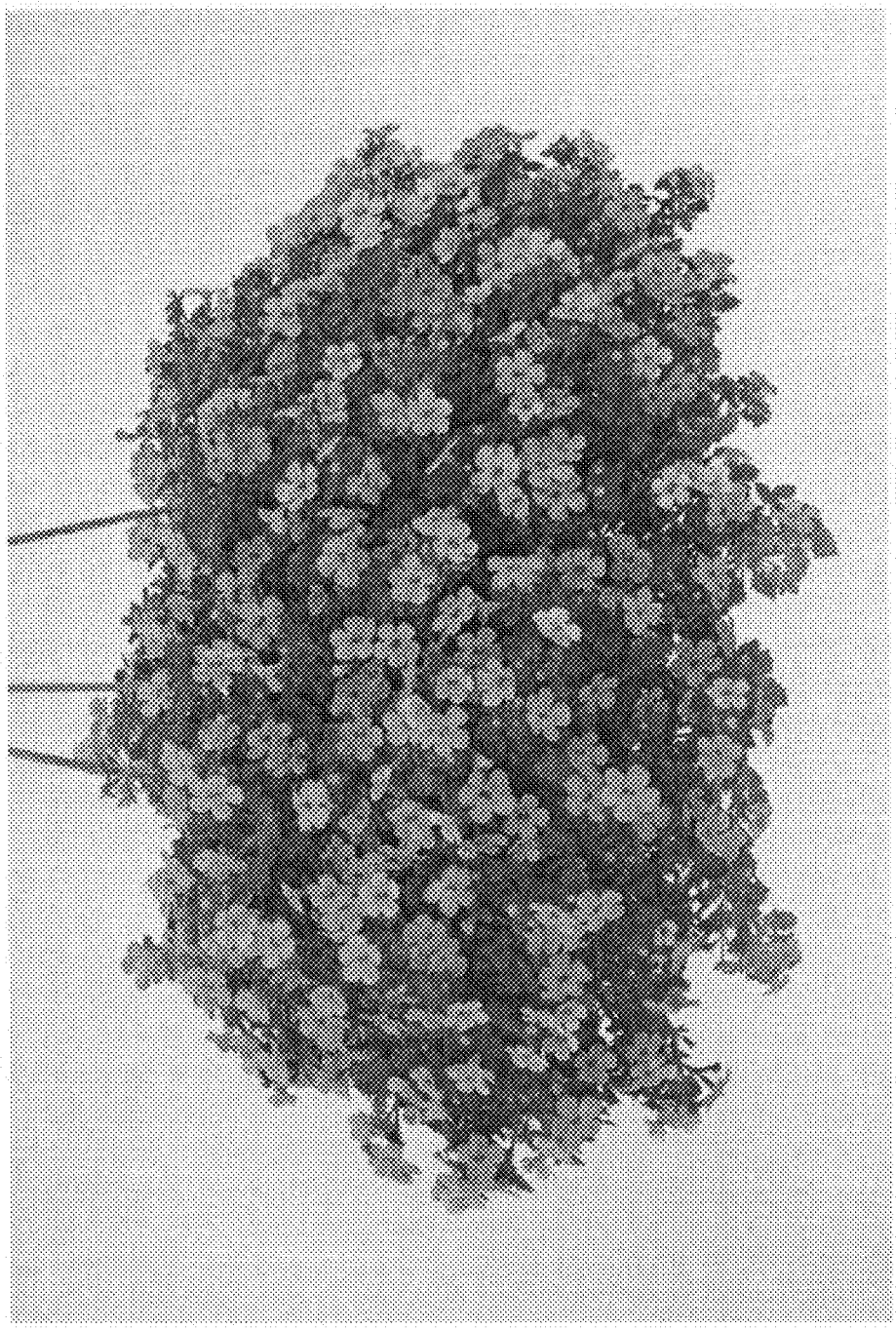

The accompanying photograph in FIG. 1 illustrates in full color a typical plant of 'DANCOP28' grown in a greenhouse, in a 16 cm basket. Age of the plant photographed is approximately 3 months from a rooted cutting.

Figure 2:
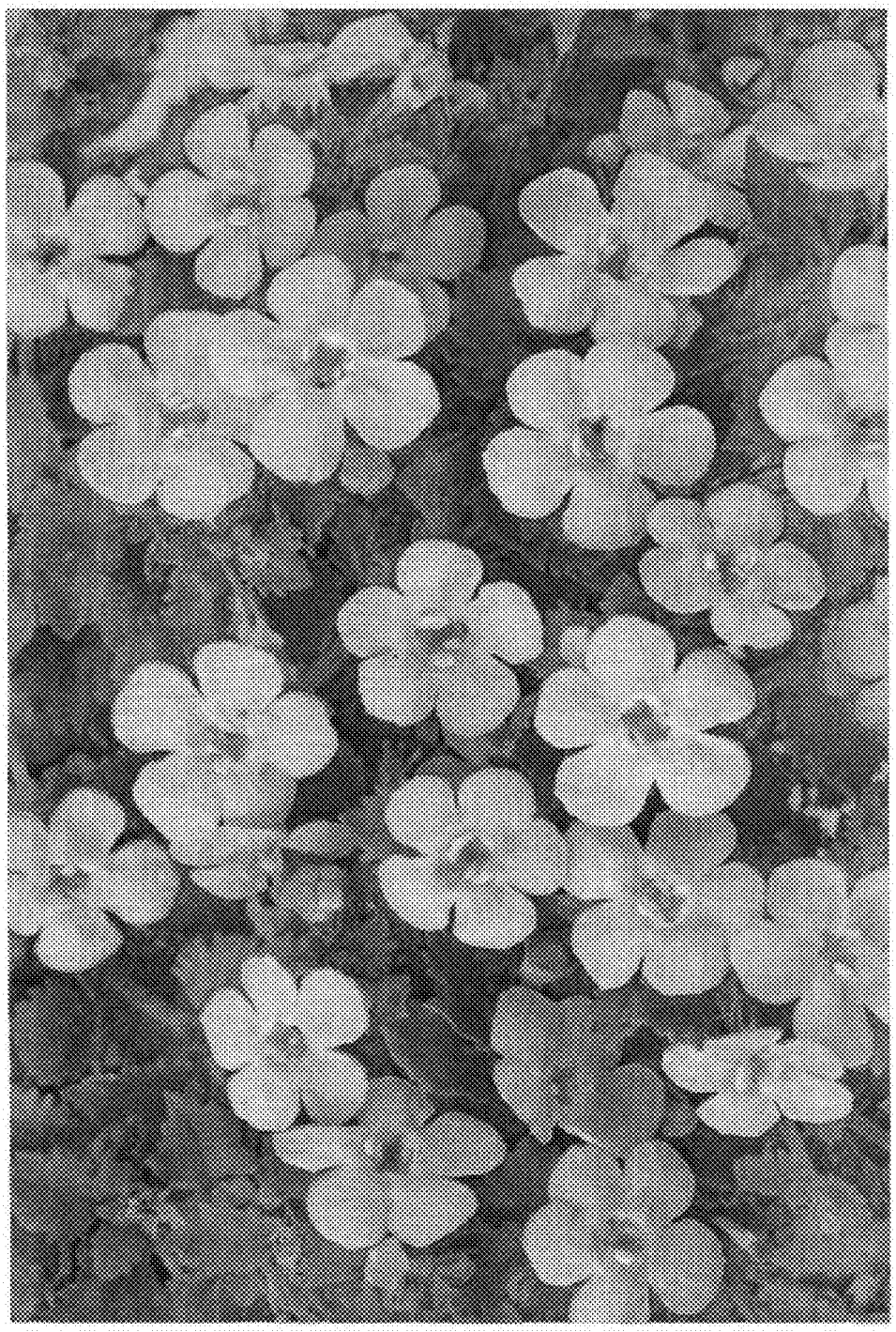

FIG. 2 illustrates in full color a close up of a typical bloom of 'DANCOP28.' The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart except where general terms of ordinary dictionary significance are used. The following observations and measurements describe 'DANCOP28' plants grown in a greenhouse in Moshav Mishmar Hashiva, Israel. The growing temperature ranged from 15° C. to 24° C. during the day and 13 to 15° C. at night. The greenhouse is un-shaded, giving bright, normal sunlight conditions. Measurements and numerical values represent averages of typical plant types.

Botanical classification: *Sutera cordata* 'DANCOP28'.

PROPAGATION

Time to initiate roots: 7 to 10 days at approximately 20° C.

Root description: Fine, fibrous roots.

PLANT

Growth habit: Semi-trailing.
Plant shape: Ball shaped.
Pot size of plant described: 16 cm.
Height: About 12 cm.
Plant spread: About 50 cm.
Growth rate: Medium.
Branching characteristics: Free branching.
Length of primary lateral branches: About 40 cm.
Diameter of lateral branches: About 0.3 cm.
Quantity of primary lateral branches: About 8.
Characteristics of primary lateral branches:
- *Form.*—Cylindrical.
- *Diameter.*—About 0.3 cm.
- *Color.*—RHS Yellow-Green 146A.
- *Texture.*—Velvety.
- *Strength.*—Strong.

Internode length: About 2 cm.

FOLIAGE

Leaf:
- *Arrangement.*—Opposite.
- *Quantity.*—Approximately 200 per primary branch.
- *Average length.*—3 cm.
- *Average width.*—2.5 cm.
- *Shape of blade.*—Ovate.
- *Apex.*—Acute.
- *Base.*—Acuminate.
- *Margin.*—Serrate.
- *Texture of top surface.*—Velvety.
- *Pubescence.*—Slight.
- *Aspect.*—Slanted upward.

Color: Young foliage upper side: Near RHS Green 137B. Young foliage under side: Near RHS Green 137C. Mature foliage upper side: Near RHS Green 137A. Mature foliage under side: Near RHS Green 137B.
- *Venation.*—Type: Pinnate. Venation color upper side: Near RHS Green 137A. Venation color under side: Near RHS Green 137A.

Petiole: Length: 0.5 cm. Diameter: 0.2 cm. Color: Near RHS Green 137A.
- *Texture: Velvety.*

FLOWER

Natural flowering season: Spring and Autumn. In moderate climates, Winter flowering as well.

Days to flowering from rooted cutting: About four weeks.

Inflorescence and flower type and habit: Inflorescence is solitary, axillary. Salverform flower type, outwardly facing.

Rate of flower opening: 1 to 2 days from bud to fully opened flower.

Flower longevity on plant: About 7 days.

Persistent or self-cleaning: Persistent.

Bud:
- *Shape.*—Spatulate.
- *Length.*—About 1.2 cm.
- *Diameter.*—About 0.6 cm.
- *Color.*—Near RHS Violet-Blue 91A.

Flower size:
- *Diameter.*—About 2.7 cm.
- *Length.*—About 1.5 cm.
- *Corolla tube diameter.*—About 0.5 cm.
- *Corolla tube length.*—About 0.7 cm.

Corolla/petals:
- *Arrangement.*—Gameopetalous.
- *Lobe length.*—About 0.8 cm.
- *Lobe width.*—About 1.1 cm.
- *Quantity.*—5.
- *Texture.*—Velvety.
- *Lobe apex.*—Rounded.
- *Lobe shape.*—Rounded.
- *Margin.*—Entire.
- *Aspect.*—Flat, right angle to the flower tube.

Color:
- *When opening.*—Upper surface: Near RHS Violet-Blue 91A. Lower surface: Near RHS Violet-Blue 91B.
- *Fully opened.*—Upper surface: Near RHS Violet-Blue 91B. Lower surface: Near RHS Violet-Blue 91C.
- *Inner corolla tube color.*—Near RHS Yellow-Orange 15A.
- *Outer corolla tube color.*—Near RHS Violet-Blue 91C.

Calyx/sepals:
- *Quantity per flower.*—5.
- *Shape.*—Linear.
- *Length.*—About 0.5 cm.
- *Width.*—About 0.1 cm.
- *Apex.*—Acute.
- *Base.*—Fused.
- *Margin.*—Entire.
- *Texture.*—Upper surface: Velvety. Lower surface: Velvety.
- *Color.*—Upper surface: Near RHS Yellow-Green 146B. Lower surface: Near RHS Yellow-Green 146B.

Peduncle: None

Pedicel:
- *Length.*—Approximately 0.7 cm.
- *Diameter.*—Approximately 0.1 cm. Color: Near RHS Yellow-Green 146B.
- *Orientation.*—Slanted upward.
- *Pubescence.*—Slight.

Fragrance: None.

REPRODUCTIVE ORGANS

Stamens:
- *Number.*—4.
- *Filament length.*—Approximately 1 cm.
- *Filament color.*—Near RHS Yellow 1C.

Anthers:

*Shape.*—Cylinder.

*Length.*—Approximately 0.1 cm.

*Color.*—Near RHS Yellow-Orange 14B.

*Pollen.*—Color: Near RHS Yellow-Orange 14B. Quantity: Moderate amount.

Pistil:

*Number.*—1.

*Length.*—About 1 cm.

*Style.*—Length: About 0.8 cm. Color: Near RHS Yellow-Green 145A.

*Stigma.*—Shape: Undulate. Color: Near RHS Yellow-Green 146C. Ovary Color: Near RHS Green 137B.

OTHER CHARACTERISTICS

Seeds and fruits: The fruit is an ellipsoid capsule, containing about 20 rounded, light brown seeds, Near RHS Grey-Brown 199C, of about 0.5 mm in size.

Disease/pest resistance: Neither resistant nor susceptible to normal *Sutera* diseases and pests.

Temperature tolerance: In the range of about 5° C.-35° C.

What is claimed is:

1. A new and distinct cultivar of *Sutera* plant named 'DANCOP28' as herein illustrated and described.

* * * * *